United States Patent [19]
Leiner et al.

[11] Patent Number: 6,165,248
[45] Date of Patent: Dec. 26, 2000

[54] EVALUATING PRECIOUS METAL CONTENT IN THE PROCESSING OF SCRAP MATERIALS

[75] Inventors: Jack Leiner, Monmouth Beach, N.J.; Gary A. Wolf, Cleveland Heights, Ohio

[73] Assignee: Metallic Fingerprints, Inc., Monmouth Beach, N.J.

[21] Appl. No.: 09/317,689

[22] Filed: May 24, 1999

[51] Int. Cl.⁷ .............................. C22B 1/14; G01N 33/20
[52] U.S. Cl. ................. 75/353; 75/376; 75/384; 75/747; 436/80; 436/84
[58] Field of Search .............. 75/353, 376, 384, 75/401, 747; 436/80, 84

[56] References Cited

U.S. PATENT DOCUMENTS

| | | |
|---|---|---|
| 3,372,993 | 3/1968 | Brown . |
| 3,733,178 | 5/1973 | Eriksen . |
| 3,772,099 | 11/1973 | Ryan et al. . |
| 3,772,200 | 11/1973 | Liversay . |
| 3,861,886 | 1/1975 | Meloy . |
| 4,478,941 | 10/1984 | Hillshafer . |
| 4,615,731 | 10/1986 | Thomas et al. ............ 75/353 |
| 4,654,165 | 3/1987 | Eisenberg . |
| 4,707,453 | 11/1987 | Wagner et al. . |
| 4,952,514 | 8/1990 | Haddad ..................... 436/84 |
| 4,966,511 | 10/1990 | Hoots et al. . |
| 5,059,261 | 10/1991 | Condo et al. . |
| 5,125,963 | 6/1992 | Alden et al. ............... 75/384 |
| 5,179,027 | 1/1993 | Fisher . |
| 5,201,921 | 4/1993 | Luttermann et al. . |
| 5,217,171 | 6/1993 | Feldman ..................... 241/24 |
| 5,324,356 | 6/1994 | Goodwin . |
| 5,397,819 | 3/1995 | Krutak et al. . |
| 5,474,937 | 12/1995 | Anderson, II et al. . |
| 5,677,186 | 10/1997 | Anderson, II et al. . |
| 5,677,187 | 10/1997 | Anderson, II et al. . |
| 5,948,137 | 9/1999 | Pflaum ..................... 75/384 |

FOREIGN PATENT DOCUMENTS

| | | | |
|---|---|---|---|
| 5-263160 | 10/1993 | Japan | ..................... 75/384 |

*Primary Examiner*—George Wyszomierski
*Attorney, Agent, or Firm*—Arthur Jacob

[57] ABSTRACT

A method for evaluating a batch of scrap material, subsequent to processing of the batch, to determine the content of precious metal present in the batch prior to processing of the batch, includes introducing a predetermined amount of a tracer into the batch, prior to processing, processing the batch and the tracer into a homogenous mixture, assaying a sample portion of the homogenous mixture to assess the amount of tracer in the sample portion, and to assess the amount of precious metal in the sample portion, and ascertaining the content of the precious metal in the batch prior to processing of the batch by applying to the assayed amount of the precious metal a ratio between the predetermined amount of tracer introduced into the batch prior to processing and the assessed amount of tracer in the sample portion. Where the precious metal includes gold, silver, platinum, palladium or rhodium, a tracer includes one or more of the metals bismuth, antimony, lead, cadmium, tellurium, barium, cobalt, nickel, hafnium and selenium.

6 Claims, No Drawings

EVALUATING PRECIOUS METAL CONTENT IN THE PROCESSING OF SCRAP MATERIALS

The present invention relates generally to the recovery of precious metals from scrap materials which bear precious metals and pertains, more specifically, to method and materials used in the method for verifying the amount of precious metal present in a batch of scrap material to be processed for recovery of the precious metal, by evaluation of a sample of the batch taken subsequent to processing the batch.

A variety of industries generate scrap materials which contain precious metals. Usually, these scrap materials are sold to scrap processors who will recover the precious metals from the scrap materials. Thus, jewelry manufacturers, semiconductor producers, precious metal plating operators and photographic processors are some of the industries which generate scrap materials bearing precious metals such as, for example, gold, silver, platinum, palladium and rhodium.

The handling and evaluation of precious metal bearing scrap material presents problems to both the seller of the scrap material and the purchaser in that neither the seller nor the purchaser can know the precise amount of precious metal in a batch of scrap material prior to processing of the batch. Often, a seller must rely upon the purchaser to report the amount of precious metal recovered from a particular batch of scrap material, leading to some uncertainty in the value of the scrap material prior to processing. This uncertainty in the value of the scrap material has created an atmosphere of skepticism, insecurity and even distrust among sellers and buyers of scrap materials.

The present invention enables determining, with a high degree of certainty, the amount of precious metal present in a given batch of scrap material prior to processing of the batch, by evaluation of a sample of the processed batch. As such, the present invention attains several objects and advantages, some of which are summarized as follows: Enables the determination, with precision, of the amount of precious metal contained within a heterogeneous mixture of scrap materials in a batch of scrap material, prior to processing the batch, by evaluating a sample of the processed scrap material; assures that all of the amount of precious metal in a batch of precious metal bearing scrap material is accounted for subsequent to processing of the batch; instills confidence in both the seller and in the purchaser of precious metal bearing scrap materials in that the value of the scrap material is verified with accuracy and reliability; deters unauthorized removal of any quantity of precious metal from precious metal bearing scrap material; provides better control over the processing of scrap materials for the recovery of constituents of the scrap material; allows a seller of scrap material bearing precious metal to assure compensation for the full value of the scrap material with relative ease and minimal expense.

The above objects and advantages, as well as further objects and advantages, are attained by the present invention which may be described briefly as a method for evaluating a batch of scrap material of known quantity, subsequent to processing of the batch, to determine the content of at least one precious metal present in the batch prior to processing of the batch, the precious metal including one or more of the metals gold, silver, platinum, palladium and rhodium, the method comprising: introducing a predetermined amount of a tracer into the batch of scrap material of known quantity, prior to processing of the batch; processing the batch of scrap material and the tracer into a homogenous mixture; assaying a sample portion of a prescribed quantity of the homogenous mixture to assess the amount of tracer in the sample portion, and to assess the amount of precious metal in the sample portion; and ascertaining the content of the precious metal in the batch of scrap material prior to processing of the batch by applying to the assayed amount of the precious metal a ratio between the predetermined amount of tracer introduced into the batch prior to processing and the assessed amount of tracer in the sample portion.

Further, the invention includes a tracer for use in evaluating a batch of scrap material of known quantity, subsequent to processing of the batch, to determine the content of precious metal present in the batch prior to processing of the batch, the precious metal including one or more of the metal gold, silver, platinum, palladium and rhodium, the tracer comprising at least one metal selected from the group consisting of bismuth, antimony, lead, cadmium, tellurium, barium, cobalt, nickel, hafnium and selenium.

Ordinarily, a seller of precious metal bearing scrap material will deliver a lot of heterogeneous scrap material of known quantity to a processor who then processes the lot to recover the precious metal. In order to evaluate a lot, the lot is processed into a homogeneous batch of scrap material and a sample portion of a prescribed quantity of the homogenous batch is assayed, either by the processor or by the seller, in order to assess the amount of precious metal in the sample portion. By directly relating the prescribed quantity of the sample portion to the known quantity of the lot of scrap material, the amount of precious metal in the lot, prior to processing the lot, and hence the value of the lot, can be calculated. Thus, if B is the weight of the lot of scrap material delivered to the processor, S is the weight of the sample portion, and $P_a$ is the weight of the precious metal actually derived from the sample portion, then the total amount P of the precious metal in the lot of scrap material can be expressed as follows:

$$P = P_a B/S$$

However, the accuracy of the amount P derived from the above expression requires that the full lot B be homogenized before a sample portion S is taken so that the calculation yields a true amount for P. Should a part of the lot be deleted prior to processing the scrap material into a homogenous batch, either deliberately or by an inaccuracy in processing, or by some other error, the amount of precious metal $P_a$ actually derived from the sample portion will be reduced, with a proportional reduction in the calculated amount P, and a concomitant reduction in the reported value of the lot of scrap material. The present invention enables detection of any discrepancy between the full amount of precious metal actually present in a batch of precious metal bearing scrap material prior to processing of the batch, and the amount of precious metal reported to be in the batch prior to processing of the batch, as a result of the assay of a sample portion of the batch subsequent to processing of the batch. The term "processing" as employed herein includes at least homogenizing the lot of scrap material, as outlined above.

In the practice of the present invention, a measured, predetermined amount of a tracer is added to a lot of scrap material bearing precious metal. The lot is delivered for processing in the form of a batch containing a heterogeneous mixture of materials, and the tracer includes at least one metal, and preferably more than one metal, not usually found in the batch. The batch then is processed to homogenize the materials in the batch. For example, metallic scrap is melted and formed into ingots which then are weighed. A sample portion in the form of a prescribed quantity of the processed batch then is assayed to determine the amount of tracer in the sample portion and to determine the amount of precious metal in the sample portion.

A ratio then is determined between the assessed amount of the tracer and an amount of the tracer expected to be found in the sample portion, based upon the predetermined amount of tracer originally placed in the batch, prior to processing of the batch, the known quantity of material in the batch prior to processing, and the prescribed quantity of material in the sample portion. The ratio then is applied to the assayed amount of the precious metal to determine the content of the precious metal in the batch of scrap material prior to processing of the batch, based upon the known quantity of material in the batch prior to processing and the prescribed quantity of material in the sample portion.

While the tracer may be a single metal not found in the scrap material, the preferred tracer is in the form of a mixture of metals, each of which metals is chosen on the basis of the chemical behavior of the tracer materials being similar to the chemical behavior exhibited by the precious metal in the scrap material when subjected to the processing techniques and evaluation procedures ordinarily conducted during the processing of the scrap material. In this manner, the tracer will "follow" the precious metal during processing so as to be present in the processed batch in the same predetermined amount as introduced to the batch prior to processing. Preferred tracers include a mixture of constituents selected from the group consisting of bismuth, antimony, lead, cadmium, tellurium, barium, cobalt, nickel, hafnium and selenium. In view of the uncertainties in the composition of any lot of scrap material, the use of a mixture of constituents in the tracer assures that at least one of the constituents, and preferably more than one, will be a metal not found in a particular lot of scrap material and will therefore serve as an accurate indicator for the purpose of auditing precious metal content of the scrap material in accordance with the present invention. One mixture found to be exceptionally effective in the practice of the present invention is made up of about 65% by weight of tellurium, about 25% by weight of bismuth and about 10% by weight of selenium. Tracers are prepared from commercially available certified pure metallic powders. The selected powders are weighed, blended together and then a sample of the blended mixture is analyzed, as by atomic absorption spectroscopy (AAS), to verify the content of the blended powders.

The manner in which a tracer is introduced into the scrap material is dependent upon the nature of the scrap material. Thus, where the scrap material is a lot of metallic scrap to be processed by melting, the tracer preferably is introduced in a jellied form prepared by mixing the blended powder mixture with petroleum jelly. The resultant jellied tracer powder is assayed to certify the content of the constituents and a measured amount of the jellied tracer powder is applied to the bulk of the scrap material and allowed to flow around all surfaces. Care is taken to assure that the amount of tracer added to the lot is known with precision. In the preferred preparation, an aliquot of blended tracer powder includes 250 grams of blended powder which is mixed with 500 grams of petroleum jelly and the resultant jellied tracer is placed into dispensing tubes for subsequent delivery. The amount of tracer introduced is governed by the lot size of the scrap material. Preferably, enough tracer is added to the lot to yield at least fifty parts per million (50 ppm) of tracer in the final processed lot.

Where the lot of scrap material is to be processed by incineration, with the resultant ash ground and screened to a homogeneous residue for sampling, the tracer preferably is delivered to the lot by combining a known weight of blended tracer powder mixture with a urethane resin and placing the combined powder mixture and urethane resin into a container, such as a commercially available plastic bag, which is then sealed for delivery to the lot of scrap material. In the preferred preparation, an aliquot of blended tracer powder includes 250 grams of blended powder, 250 grams of urethane resin is added to the aliquot, and the combined blended powder and urethane resin is sealed in the plastic bag for delivery. A jellied tracer, as described above, also may be used in connection with the lot. Preferably, enough tracer is added to the lot to yield at least one hundred parts per million (100 ppm) of tracer in the residue.

Where the lot of scrap material is a solution which is to be sampled as a solution, the tracer preferably is delivered in the form of a tracer solution. An aliquot of blended tracer powder is dissolved in warm concentrated nitric acid. The resultant solution is diluted with deionized water, sampled to verify content, and then sealed in ampules for delivery. In the preferred preparation, the aliquot of blended tracer powder includes 150 grams of blended powder and the dissolved powder is diluted to one liter, into which one mole of NaCN has been dissolved, and the solution is sealed within 100 ml. ampules. Upon delivery, the tracer solution is added to the lot of scrap material. The preferred concentration of tracer solution in the lot of scrap material is at least 100 cc. (one ampule) per 100 gallons of scrap material.

Subsequent to processing a batch of scrap material to which a tracer has been added, as described above, a sample portion comprised of a prescribed quantity of the material of the processed batch is assayed for tracer content and either the same sample or another sample of the processed batch is assayed for precious metal content. In one method, the tracer is assayed by inductively coupled plasma spectroscopy (ICP) analysis of a solution derived from nitric acid leaching. In an alternate method, atomic absorption spectroscopy (AAS) is used to assay the solution derived from nitric acid extraction of the sample. In either method, the extraction is proven to be quantitative.

Once the actual amount of tracer in the sample portion is ascertained, a ratio R is determined between an amount of tracer expected to be found in the sample portion, based upon the predetermined amount of the tracer, the known quantity of material in the batch prior to processing, and the prescribed quantity of material in the sample portion assayed for the tracer, and the actual amount of tracer found in the sample portion. Thus, if T is the weight of the predetermined amount of tracer delivered to the batch of scrap material prior to processing of the batch, $T_e$ is the weight of tracer expected to be found, and $T_a$ is the weight of tracer actually found in the assayed sample, and if B is the weight of the known amount of material in the batch prior to processing and S is the weight of the prescribed amount of the sample portion assessed for tracer, then the ratio R is $T_e/T_a$ where $T_e = T\ S/B$. If the weight ($T_a$) of tracer actually found in the assayed sample matches the weight ($T_e$) of tracer expected to be found, then the ratio R is 1, confirming that the actual amount of precious metal in the batch, prior to processing, can be determined directly from the amount of precious metal derived from an assay of a sample of prescribed quantity, on the basis of a comparison of that prescribed quantity with the known amount of material in the batch prior to processing, as described above. However, if the ratio R is greater than 1, that is, if the weight ($T_a$) of tracer actually found falls short of the weight ($T_e$) of tracer expected to be found in the assayed sample portion, that becomes an indication that there is a shortage of precious metal in the processed batch of material. Should a shortage be detected, an investigation can be made into whether the shortage is a result of inadvertent processing errors or deliberate acts occurring between submission of the lot of scrap material for processing and the taking of a sample portion subsequent to processing of a batch.

Using the ratio R, the true, full precious metal content of the batch, prior to processing, can be determined. Thus, if $P_a$ is the weight of the precious metal actually derived from assaying a sample portion of prescribed quantity S of the material of the batch, then the full amount $P_f$ of precious metal in the batch prior to processing can be derived on the basis of the weight B of the known quantity of material in the batch prior to processing, the prescribed quantity S of material in the sample portion, and the ratio R. Hence, the full amount of precious metal in the batch prior to processing can be expressed as follows:

$$P_f = R\, P_a\, B/S, \text{ or}$$

$$P_f = P_a\, T/T_a$$

Accordingly, through the use of a tracer, as described above, a seller of scrap material can determine, through analysis of a sample portion of the scrap material taken subsequent to processing, the amount of precious metal in the batch of scrap material prior to processing. For example, where a seller of precious metal bearing scrap material introduces a tracer into a lot of scrap material and then delivers the lot of scrap material to a processor, the processor will return a sample portion of the processed lot to the seller. The seller then can assay the sample portion for precious metal and for the tracer introduced by the seller into the lot, thereby auditing the lot for an accurate determination of the amount of precious metal in the lot prior to delivery of the lot to the processor. Any shortage of precious metal indicated by the analysis of the sample portion then can be investigated to determine if the shortage is a result of deliberate removal of precious metal content, of processing errors or some other inaccuracies in the processing of the scrap material. In any event, the procedure enables an accurate determination of the amount of precious metal present in the lot of scrap material prior to delivery of the lot to the processor.

The following examples demonstrate the practice of the present invention:

EXAMPLE 1

A batch of scrap material of known quantity in the form of a heterogenous mixture of scrap metal having a weight of 1000 kg was processed for recovery of an unknown amount of precious metal content. Prior to processing, 100 grams of a tracer was added to the batch. The tracer included a mixture of 65% by weight of tellurium, 25% by weight of bismuth and 10% by weight of selenium. The known quantity of scrap metal in the batch, together with the predetermined amount of tracer, then was melted to form a homogenous mixture of constituents. A sample portion of 31.1 grams of the homogenous mixture was assayed and found to include 3.11 grams of precious metal in the form of gold, together with 6.5 ppm of tellurium, 2.5 ppm of bismuth and 1.0 ppm of selenium.

Based solely upon the actual weight of gold found in the assay of the sample portion, the weight of the sample portion itself, and the weight of the known quantity of scrap metal in the batch, the amount of gold ($P_i$) indicated to be in the batch prior to processing can be calculated as follows:

$$P_i = P_a\, B/S$$

The ratio R is determined as follows:

$$R = T_e/T_a \text{ where } T_e \text{ is } T\, S/B \text{ so that}$$

$$R = 1.$$

The full amount of gold in the batch prior to processing is derived as follows:

$$P_f = R\, P_a\, B/S = 100 \text{ kg; or}$$

$$P_f = P_a\, T/T_a = 100 \text{ kg.}$$

Thus, the assay of the sample subsequent to processing of the batch confirms that the amount of gold in the batch, prior to processing, indeed was 100 kg and that all of the gold is present in the homogenized mixture.

EXAMPLE 2

A batch of scrap material of known quantity in the form of a heterogenous mixture of scrap metal having a weight of 1000 kg was delivered for processing for recovery of an unknown amount of precious metal content. Prior to processing, 100 grams of a tracer was added to the batch. The tracer included a mixture of 65% by weight of tellurium, 25% by weight of bismuth and 10% by weight of selenium. Subsequent to adding the tracer, 50 kg of the batch of scrap material deliberately was removed and set aside. The remaining quantity of scrap metal in the batch, together with the predetermined amount of tracer, then was melted to form a homogenous mixture of constituents. A sample portion of 31.1 grams of the homogenous mixture was assayed and found to include 2.954 grams of gold, together with 6.17 ppm of tellurium, 2.37 ppm of bismuth and 0.95 ppm of selenium.

Based solely upon the actual weight of gold found in the assay of the sample portion, the weight of the sample portion itself, and the weight of the known quantity of scrap metal in the batch, the amount of gold ($P_i$) indicated to be in the batch prior to processing can be calculated as follows:

$$P_i = P_a\, B/S = 94.983 \text{ kg}$$

The ratio R is determined as follows:

$$R = T_e/T_a \text{ where } T_e \text{ is } T\, S/B \text{ so that}$$

$$R = 1.053$$

The full amount of gold in the delivered batch prior to processing is derived as follows:

$$P_f = R\, P_a\, B/S = 100 \text{ kg; or}$$

$$P_f = P_a\, T/T_a = 100 \text{ kg.}$$

Thus, the assay of the sample subsequent to processing of the batch revealed a discrepancy between the amount of gold indicated to be in the delivered batch, prior to processing, and the full amount of gold determined by applying to the assayed amount of gold ($P_a$) a ratio between the predetermined amount of tracer (T) introduced into the batch prior to processing and the assessed amount of tracer ($T_a$) in the sample portion, demonstrating that not all of the gold was present in the processed homogenized mixture from which the sample portion was taken. The discrepancy introduced by deliberate removal of a portion of the delivered batch was detected and the true value of the delivered batch is ascertained.

It will be seen that the present invention attains the objects and advantages summarized above, namely: Enables the determination, with precision, of the amount of precious metal contained within a heterogeneous mixture of scrap materials in a batch of scrap material, prior to processing the batch, by evaluating a sample of the processed scrap material; assures that all of the amount of precious metal in a batch of precious metal bearing scrap material is accounted for subsequent to processing of the batch; instills confidence in both the seller and in the purchaser of precious metal bearing scrap materials in that the value of the scrap material is verified with accuracy and reliability; deters unauthorized removal of any quantity of precious metal from precious metal bearing scrap material; provides better control over the processing of scrap materials for the recovery of constituents of the scrap material; allows a seller of scrap material bearing precious metal to assure compensation for the full value of the scrap material with relative ease and minimal expense.

It is to be understood that the above detailed description of preferred embodiments of the invention is provided by way of example only. Various details of procedure and composition may be modified without departing from the true spirit and scope of the invention, as set forth in the appended claims.

The embodiments of the invention in which an exclusive property or privilege is claimed are defined as follows:

1. A method for evaluating a batch of scrap material of known quantity, subsequent to processing of the batch, to determine the content of at least one precious metal present in the batch prior to processing of the batch, the precious metal including one or more of the metals gold, silver, platinum, palladium and rhodium, the method comprising:

introducing a known amount of a tracer into the batch of scrap material of known quantity, prior to processing of the batch;

processing the batch of scrap material and the tracer into a homogenous mixture;

assaying a sample portion of a prescribed quantity of the homogenous mixture to assess the amount of tracer in the sample portion, and to assess the amount of precious metal in the sample portion; and ascertaining the content of the precious metal in the batch of scrap material prior to processing of the batch by applying to the assayed amount of the precious metal a ratio between the known amount of tracer introduced into the batch prior to processing and the assessed amount of tracer in the sample portion.

2. The method of claim 1 wherein the tracer includes at least one element not found in the batch of scrap material.

3. The method of claim 2 wherein the element of the tracer is selected from the group consisting of bismuth, antimony, lead, cadmium, tellurium, barium, cobalt, nickel, hafnium and selenium.

4. The method of claim 2 wherein the tracer includes a mixture of elements selected from the group consisting of bismuth, antimony, lead, cadmium, tellurium, barium, cobalt, nickel, hafnium and selenium.

5. The method of claim 2 wherein the tracer includes a mixture of tellurium, bismuth and selenium.

6. The method of claim 2 wherein the tracer includes a mixture of 65% by weight of tellurium, 25% by weight of bismuth and 10% by weight of selenium.

* * * * *